US005772636A

United States Patent [19]
Brimhall et al.

[11] Patent Number: 5,772,636
[45] Date of Patent: Jun. 30, 1998

[54] CATHETER ASSEMBLY WITH INTERLOCKING TELESCOPING NEEDLE SHIELD

[75] Inventors: Greg L. Brimhall, West Jordan; Christopher P. Steinman, Sandy, both of Utah

[73] Assignee: Becton Dickinson and Company, Franklin Lakes, N.J.

[21] Appl. No.: 756,924

[22] Filed: Dec. 2, 1996

[51] Int. Cl.$^6$ .................................................. A61M 5/32
[52] U.S. Cl. ........................ 604/198; 604/164; 604/192; 604/263
[58] Field of Search ................................... 604/110, 117, 604/164, 165, 171, 192, 198, 263, 264, 280

[56] References Cited

U.S. PATENT DOCUMENTS

| | | | |
|---|---|---|---|
| 3,867,937 | 2/1975 | Schwartz | 128/221 |
| 3,994,295 | 11/1976 | Wulff | 128/215 |
| 4,702,737 | 10/1987 | Pizzino | 604/191 |
| 4,725,267 | 2/1988 | Vaillancourt | 604/192 |
| 4,747,831 | 5/1988 | Kulli | 604/110 |
| 4,762,516 | 8/1988 | Luther et al. | 604/164 |
| 4,804,372 | 2/1989 | Laico et al. | 604/198 |
| 4,813,940 | 3/1989 | Parry | 604/198 |
| 4,832,696 | 5/1989 | Luther et al. | 604/164 |
| 4,834,718 | 5/1989 | McDonald | 604/195 |
| 4,846,805 | 7/1989 | Sitar | 604/165 |
| 4,846,811 | 7/1989 | Vanderhoof | 604/263 |
| 4,892,521 | 1/1990 | Laico et al. | 604/192 |
| 4,894,055 | 1/1990 | Sudnak | 604/198 |
| 4,897,083 | 1/1990 | Martell | 604/192 |
| 4,915,702 | 4/1990 | Haber | 604/198 |
| 4,921,491 | 5/1990 | Champ | 604/199 |
| 4,927,416 | 5/1990 | Tomkiel | 604/198 |
| 4,935,013 | 6/1990 | Haber et al. | 604/192 |
| 4,944,728 | 7/1990 | Carrell et al. | 604/164 |
| 4,950,250 | 8/1990 | Haber et al. | 604/192 |
| 4,950,252 | 8/1990 | Luther et al. | 604/198 |
| 4,973,317 | 11/1990 | Bobrove | 604/198 |
| 4,978,344 | 12/1990 | Dombrowski et al. | 604/198 |
| 4,994,041 | 2/1991 | Dombrowski et al. | 604/164 |
| 5,011,479 | 4/1991 | Le et al. | 604/198 |
| 5,013,305 | 5/1991 | Opie et al. | 604/192 |
| 5,057,088 | 10/1991 | Narayanan et al. | 604/198 |
| 5,104,384 | 4/1992 | Parry | 604/192 |
| 5,106,379 | 4/1992 | Leap | 604/198 |
| 5,181,524 | 1/1993 | Wanderer et al. | 128/764 |
| 5,219,338 | 6/1993 | Haworth | 664/198 |
| 5,242,416 | 9/1993 | Hutson | 604/192 |
| 5,273,540 | 12/1993 | Luther et al. | 604/110 |
| 5,295,975 | 3/1994 | Lockood, Jr. | 604/198 |
| 5,304,136 | 4/1994 | Erskine et al. | 604/110 |
| 5,332,092 | 7/1994 | Fischer | 206/365 |
| 5,334,149 | 8/1994 | Nortman et al. | 604/110 |
| 5,336,199 | 8/1994 | Castillo et al. | 604/198 |
| 5,374,252 | 12/1994 | Banks et al. | 604/158 |
| 5,376,075 | 12/1994 | Haughton et al. | 604/158 |
| 5,419,766 | 5/1995 | Chang et al. | 604/110 |
| 5,456,668 | 10/1995 | Ogle II | 604/110 |
| 5,472,430 | 12/1995 | Vaillancourt et al. | 604/198 |
| 5,531,713 | 7/1996 | Mastronardi et al. | 604/263 |

FOREIGN PATENT DOCUMENTS

| | | |
|---|---|---|
| 0 576 302 A1 | 12/1993 | European Pat. Off. . |
| 0 578 367 A1 | 12/1994 | European Pat. Off. . |
| 93/11816 | 6/1993 | WIPO . |

*Primary Examiner*—Sam Rimell
*Assistant Examiner*—Robert V. Racunas
*Attorney, Agent, or Firm*—Eric M. Lee

[57] ABSTRACT

A catheter and introducer needle assembly is provided wherein the catheter includes a side port and a plug located in the catheter hub, the needle is notched and is securely mounted to a shield housing with a plurality of telescoped tubes concentrically surrounding the needle. One of the telescoped tubes is securely connected to the shield housing. The other tubes in the assembly may be slid with respect to one another and distally away from the shield housing. The tubes have combined lengths to enable complete shielding of the needle when the tubes are telescopingly extended. The tubes include interlocking mechanisms to prevent separation of the tubes and to prevent collapse of the tubes once they have been fully extended. The distal-most tube, when the tubes are telescopingly extended, engages a catheter hub to prevent withdrawal of the needle from the shield assembly until the tubes are fully telescopingly extended. After the needle is fully shielded, the shielded needle is separated from the catheter hub.

13 Claims, 6 Drawing Sheets

CATHETER ASSEMBLY WITH INTERLOCKING TELESCOPING NEEDLE SHIELD

BACKGROUND OF THE INVENTION

The subject invention relates to a "bloodless" catheter assembly that includes a needle shield assembly that will safely shield the sharp distal tip of the introducer needle after the needle has been used.

Catheters, particularly intravenous (IV) catheters, are used for directing fluid into or withdrawing fluid from a patient. The most common type of IV catheter is an over-the-needle IV catheter. As its name implies, an over-the-needle IV catheter is mounted over an introducer needle having a sharp distal tip. With the distal tip of the introducer needle extending beyond the distal tip of the IV catheter, the assembly is inserted through the patient's skin into a vein. Once placement of the assembly in the vein is verified by flashback of blood in the needle, the needle is withdrawn leaving the IV catheter in place. The proximal end of the IV catheter typically has a hub that is designed to be connectable to an IV fluid supply line after insertion of the IV catheter in a patient. During the period between needle withdrawal and connection of the IV catheter to an IV fluid supply line, blood from the patient's vein can leak from the catheter.

In recent years, there has been great concern over the contamination of clinicians with a patient's blood and the immediate disposal of needles after use. This concern has arisen because of the advent of currently incurable and fatal diseases, such as Acquired Immune Deficiency Syndrome ("AIDS"), which can be transmitted by the exchange of body fluids from an infected person to another person. Thus, contact with the body fluid of an AIDS infected person must be avoided. Unfortunately, if a needle has been used to place a catheter in the vein of an AIDS infected person, the needle is a vehicle for the transmission of the disease. And a needlestick provides an immediate transmission of infected body fluid into the non-infected person. Thus, it is extremely important to minimize blood leakage during clinical procedures and for a medical technician to properly dispose of the needle to avoid a needlestick with the contaminated needle. Unfortunately, in certain medical environments, such as emergency situations or as a result of inattention or negligence, blood leakage and needlesticks with a contaminated needle still occur.

Currently available IV catheters could be improved. For example, typical IV catheters are a source for the effluence of blood. Once the introducer needle has been removed from the catheter, there is no obstacle to the flow of blood out of the catheter. In addition, typical catheters and introducer needle assemblies have a flashback chamber at the proximal end of the needle that allows the clinician to verify that the distal end of the needle and catheter are in the vein. Unfortunately, this location for the flashback chamber requires the clinician to divert her attention away from the venipuncture site. Similarly, some needle shields have already been designed but are not completely satisfactory. Some shields only cover the sharp distal tip of the needle. This is unsatisfactory in most instances because the shaft of the needle can be the source of contamination from body fluids. Other designs that cover the entire needle shaft as well as the sharp distal tip of the needle are inadequate because they are bulky, difficult to use or require special features to be operative.

Thus, there still remains a need to provide an IV catheter assembly that is "bloodless" and facilitates verification of venipuncture as well as provide a needle shield assembly that is simple and easy to use and that completely covers the entire needle after use, as well as the sharp distal tip of the needle, and that is compact, simple and easy to use and that requires no special features.

SUMMARY OF THE INVENTION

It is therefore an object of this invention to provide a "bloodless" IV catheter.

It is another object of this invention to provide an IV catheter that facilitates verification of venipuncture.

It is still another object of this invention to provide a needle shield assembly that completely covers the entire needle as well as the sharp distal tip of the needle after use.

It is a further object of this invention to provide a needle shield assembly that is compact.

It is still a further object of this invention to provide a needle shield assembly that is simple and easy to use.

It is an even further object of this invention to provide a needle shield assembly that requires no special features or technique to be operative.

The IV catheter assembly of this invention includes an elastomeric plug in a proximal portion of the catheter hub and a side port extending from the catheter hub at a location distal to the elastomeric plug. The introducer needle has at least one notch, and preferably a pair of notches, located along a distal portion thereof. The notch allows blood to flow from the distal tip of the needle, through the needle lumen and out of the notch into the catheter hub, through the side port and into a translucent extension tube. In this way, the clinician can visualize flashback of blood when the distal tip of the introducer needle has been inserted into a patient's vein. If the catheter tube itself is translucent, the clinician can visualize flashback of blood along the distal portion of the assembly.

The needle shield assembly of this invention includes a plurality of tubes concentrically overlapping one another, i.e. nested. One tube in the shield assembly is securely affixed at its proximal end to the needle hub which is connected to the proximal end of the needle. The other tubes in the needle shield assembly can be telescoped distally relative to one another and relative to the needle hub. The tubes are dimensioned such that the needle shield assembly surrounds the distal tip of the needle when the tubes are telescopingly extended in a distal direction. Interlocking means between each adjacent tube prevents complete separation of the tubes from one another as they are extended distally and lock the tubes in the extended position to prevent re-exposure of the sharp distal tip of the needle. The distal-most tube of the extended needle shield assembly may include a tip guard securely mounted therein and biased against the needle. The tip guard will slide along the shaft of the needle as the tubes of the needle shield assembly are extended. After sufficient extension, the tip guard will pass distally beyond the distal tip of the needle, and will move toward an unbiased condition over the distal tip of the needle. Thus, the tip guard covers the sharp distal tip of the used needle and provides another mechanism to prevent re-exposure of the sharp distal tip of the used needle.

The tubes are thin-walled, but are sufficiently rigid to prevent kinking and to ensure smooth telescoping movement. The distal tubes can nest inside the proximal tubes or the distal tubes can nest outside the proximal tube. Where the distal tubes nest outside the proximal tubes, the outermost tube may be thicker than the others to protect and support the inner, thinner tubes. The thicker outer-most tube may be the tube that telescopes over the distal portion of the needle. Thus, this thicker outer tube provides accurate and efficient support for the above described tip guard therein. The outer-most tube may be releasably engaged with the catheter hub so that the collapsed shield assembly is effectively enclosed between the needle hub and the catheter hub. This presents a compact catheter and introducer needle shield assembly.

After introduction of the catheter into the patient, the needle is removed from the patient in the conventional manner. The elastomeric plug in the catheter hub prevents blood from escaping from the proximal opening in the catheter hub. Instead, the blood will be forced to flow through the extension tube which may be placed in communication with other fittings and tubes to prevent blood spillage. Proximal movement of the needle hub and needle causes the tubes of the needle shield assembly to telescopingly extend relative to one another since the outer-most tube is releasably engaged with the catheter adapter. The interlocking means lock the tubes in the extended position with respect to one another and prevent complete separation of the tubes. Thus, the needle is gradually and automatically shielded as it is withdrawn from the patient and from the catheter hub. After telescoping extension of the tubes in the shield assembly, the tip guard in the outer-most tube moves toward an unbiased condition over the distal tip of the needle. Further proximally directed forces on the needle hub will separate the outer-most tube from the catheter hub. Thus, the entire needle is safely shielded to protect the clinician from accidental needle sticks or touch contamination with body fluids that may be present within the lumen of the needle. Re-exposure of the needle by telescopingly collapsing the tubes is prevented by the interlocking means between adjacent tubes and by the tip guard. Additionally, re-exposure of the used needle by separating the telescoped tubes is prevented by the interlocking means between adjacent tubes. The shielded needle thereafter may be discarded in an appropriate receptacle.

BRIEF DESCRIPTION OF THE DRAWINGS

The preferred embodiments are illustrated in the drawings in which like reference numerals refer to like elements and in which.

DETAILED DESCRIPTION OF THE INVENTION

Figure 1:
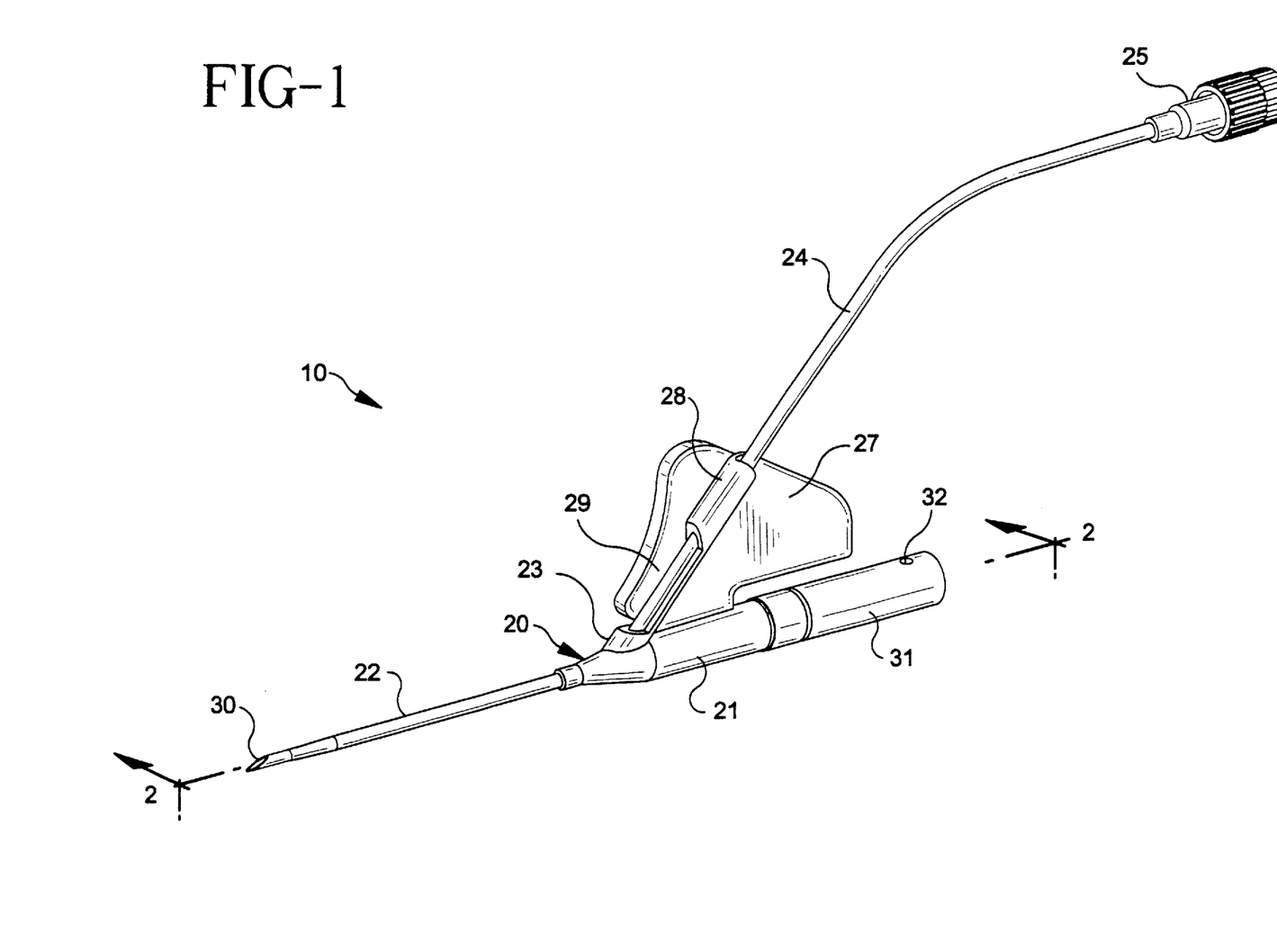
FIG. 1 is a perspective view of the IV catheter and interlocking telescoping needle shield assembly of this invention.
Figure 2:
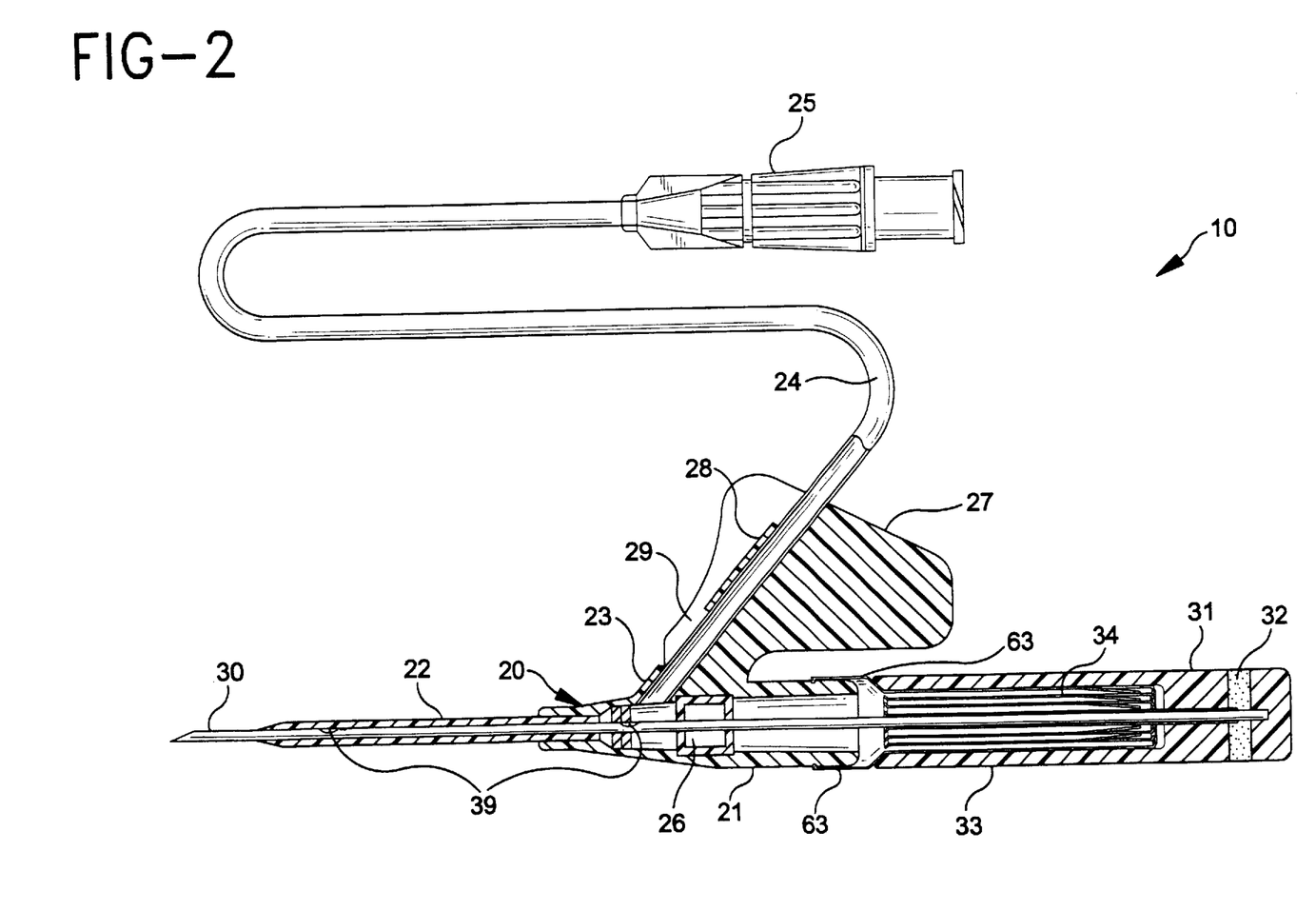
FIG. 2 is a cross-sectional view of the IV catheter and interlocking telescoping needle shield assembly of FIG. 1 without the tip guard.
Figure 3:
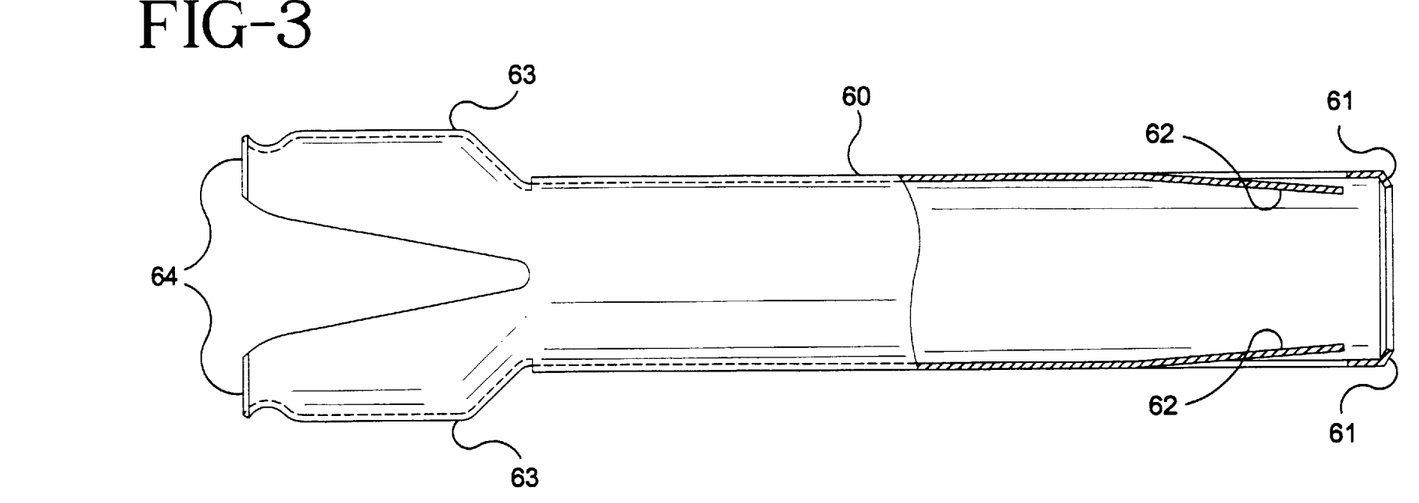
FIG. 3 is a cross-sectional view of the coupler tube that is coupled to the catheter hub.
Figure 4:
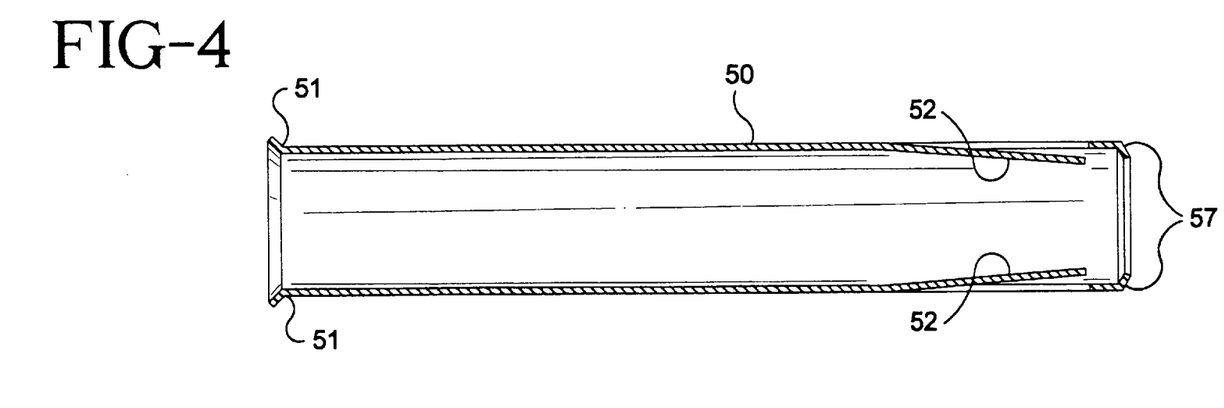
FIG. 4 is a cross-sectional view of an intermediate tube.
Figure 5:
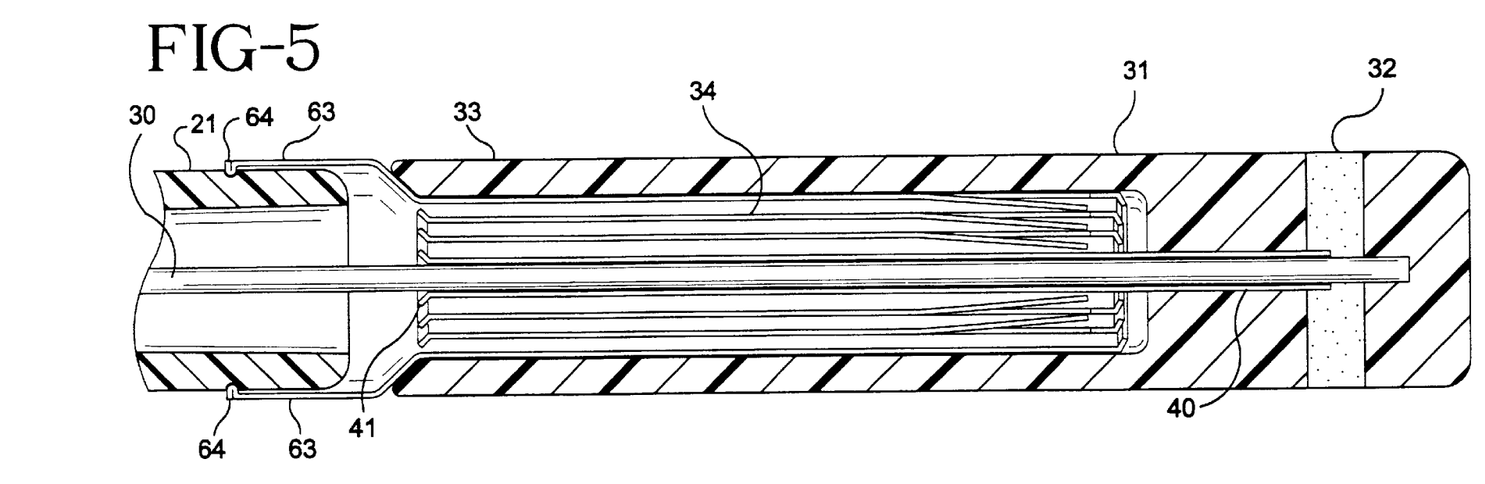
FIG. 5 is a cross-sectional view of the interlocking telescopic needle shield assembly in the compact, non-activated position without the tip guard.

The catheter assembly with the interlocking telescopic needle shield assembly in accordance with the subject invention is identified generally by the numeral 10 in FIGS. 1 and 2.

The catheter assembly 20 includes a catheter hub 21 connected to a catheter 22. The proximal end of catheter hub 21 is sealed with an elastomeric plug 26, such as polyisoprene, (See FIG. 2) to ensure that fluid does not leak out of the proximal end of catheter hub 21. Catheter hub 21 includes a side port 23 which has an extension tube 24 connected thereto located toward the distal portion of catheter hub 21. The proximal end of extension tube 24 includes a standard luer lock adapter 25 to allow the connection of an IV fluid supply line (not shown) to extension tube 24. Such an IV fluid supply line can be connected to extension tube 24 prior to insertion of catheter assembly 20 into a patient. Side port 23 is in fluid communication with the lumen of catheter 22 so that fluid infused through extension tube 24 will pass into the patient once catheter 22 is properly positioned in the patient. Conversely, blood exiting a patient's vein through catheter 22 can travel through extension tube 24. In this manner, once venipuncture has been accomplished, blood will flow through extension tube 24 to the IV fluid supply line but not through the proximal end of catheter hub 21 to render catheter assembly 20 "bloodless."

Catheter hub 21 also includes a wing 27 that extends radially from catheter hub 21. Wing 27 is generally aligned with the longitudinal axis of catheter 22. Wing 27 should be large enough to be grasped easily by a clinician. The forward or distal end of wing 27 defines a tubular member 28. Preferably tubular member 28 does not extend the full length of the distal end of wing 27. Extension tube 24 fits through tubular member 28 and into communication with side port 23. The space between side port 23 and tubular member 28 defines a window 29 that allows the clinician to observe the distal portion of extension tube 24. At least that part of extension tube 24 that extends past window 29 is formed from polyvinyl chloride so that it is translucent or transparent in window 29.

Needle 30 includes at least one notch, and preferably a pair of notches 39, that provide fluid communication between the inside and outside of needle 30. See FIG. 2. When needle 30 is located inside catheter 22 so that its distal tip extends beyond the distal tip of catheter 22, both notches 39 are distal of elastomeric plug 26. In this orientation, once venipuncture has been accomplished blood will flow into needle 30 and through notches 39. If catheter 22 is transparent or at least translucent, blood can be observed along catheter 22 so the clinician will not have to divert his or her attention from the distal portion of the assembly 10 and the site of the venipuncture to verify blood flashback. In addition, flashback of blood can be observed in window 29. Window 29 is not necessary where tubular member 28 is made of a clear material such as polycarbonate. In such a case, flashback of blood through extension tube 24 can be seen through tubular member 28.

The proximal end of needle 30 is securely adhered in a shield housing 31 in the standard manner using a sidehole glue port 32 in shield housing 31. Because the proximal end of needle 30 is sealed, blood cannot exit or leak out during use. Shield housing 31 further includes a generally hollow distal portion 33 which extends to a location intermediate the proximal and the distal ends of needle 30. Hollow distal portion 33 defines a shield cavity 34 therein which is radially dimensioned to receive the interlocking tubes as explained further herein.

The interlocking telescoping tubes are mounted concentrically around needle 30 and are initially disposed substantially within shield cavity 34. The anchor tube 40 has a proximal end projecting proximally into shield housing 31 beyond shield cavity 34 and into glue port 32. The distal end of anchor tube 40 includes an outwardly extending locking flange 41 for cooperatively locking with another of the interlocking telescoping tubes as explained further herein.

Figure 7:
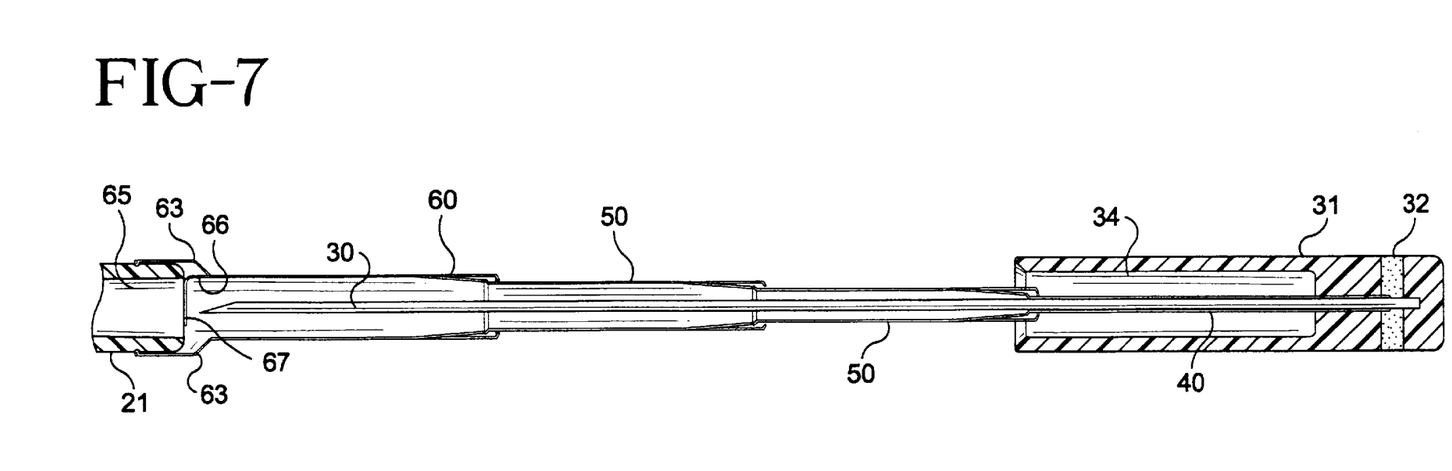
FIG. 7 is a cross-sectional view of the interlocking telescoping needle shield assembly of this invention showing the needle in a shielded condition prior to separation from the catheter hub with the tip guard in its unbiased condition shielding the tip of the needle.
Figure 9:
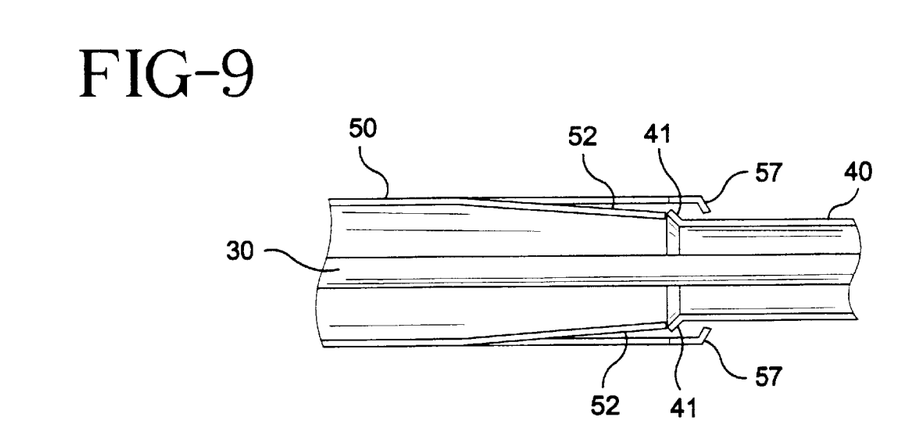
FIG. 9 is a cross-sectional view of a portion of the interlocking telescoping needle shield assembly of this invention showing the interlocking means between e.g. an intermediate tube and the anchor tube.

Intermediate tubes 50 are concentrically disposed over anchor tube 40 and can be slid distally relative to anchor tube 40 and into the position shown in FIG. 7. The proximal end of intermediate tube 50 includes an inwardly extending locking flange 57 which is dimensioned to engage outwardly extending locking flange 41 of anchor tube 40 for preventing complete separation between anchor tube 40 and intermediate tube 50 when they are extended relative to one another. See FIG. 9. The proximal end of intermediate tube 50 also includes at least one, and preferably two, lanced protrusions 52 formed therein using a standard lancing process for thin walled metal tubes. This lanced protrusion 52 is biased radially inwardly so that when intermediate tube 50 is extended with respect to anchor tube 40, so that locking flange 51 is adjacent to locking flange 41, the proximal end of lanced protrusion 52 abuts the distal face of locking flange 41. In this manner, once intermediate tube 50 has been fully extended with respect to anchor tube 40, lanced protrusion 52 prevents intermediate tube 50 from being moved proximally past anchor tube 40. Lanced protrusion 52 is sufficiently flexible to ride over locking flange 41 when intermediate tube 50 is being extended with respect to anchor tube 40. Depending on the length of needle 30, any number of intermediate tubes 50 may be used to ensure that the shield assembly can completely cover needle 30, when the shield assembly is in the fully extended position. It is to be understood that the above description and mechanisms apply to the connection and interrelationship between two intermediate tubes 50.

Anchor tube 40 and intermediate tube 50 have thicknesses selected to prevent kinking during a shielding operation, and to ensure smooth telescoping movement. However, neither anchor tube 40 nor intermediate tube 50 will directly contact the sharp distal tip of needle 30, and hence a small thickness is acceptable. Preferably stainless steel is used as the material. A wall thickness in the range of 0.002 inches to 0.007 inches is preferred for anchor tube 40 and intermediate tube 50.

The shield assembly further includes a coupler tube 60 concentrically disposed over intermediate tube 50. Coupler tube 60 can be slid distally and into the position shown in FIG. 7. The proximal end of coupler tube 60 includes an inwardly extending locking flange 61 for lockingly engaging outwardly extending locking flange 51 of intermediate tube 50. These flanges prevent complete separation between coupler tube 60 and intermediate tube 50 similar to the mechanism used to prevent complete separation between anchor tube 40 and intermediate tube 50. As with intermediate tube 50, coupler tube 60 includes at least one, and preferably two, inwardly biased lanced protrusions 62. These lanced protrusions cooperate with outwardly extending flange 51 of intermediate tube 50 to prevent coupler tube 60 from being moved proximally with respect to intermediate tube 50 similar to the mechanism used to prevent movement between anchor tube 40 and intermediate tube 50.

The distal end of coupler tube 60 is formed to include a plurality of flexible fingers 63. Preferably four such fingers 63 are formed thereon. These fingers 63 are designed to firmly grasp catheter hub 21 and thus hold the shield assembly and the catheter assembly together. Preferably each finger 63 is formed with an inwardly extending portion 64 along its distal portion. The inwardly extending portion 64 engages a groove formed around the circumference of catheter hub 21. This arrangement ensures that the shield assembly will be securely but removably engaged with catheter assembly 20.

Figure 6:
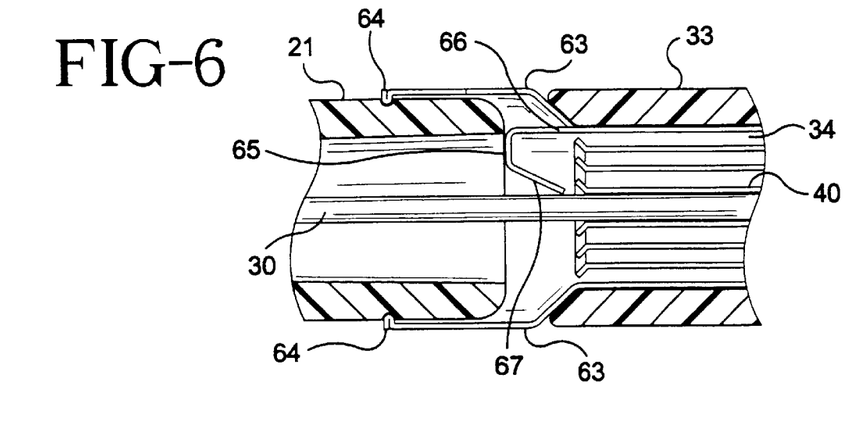
FIG. 6 is a cross-sectional view of a portion of the interlocking telescoping needle shield assembly of this invention showing the coupler tube coupled to the catheter hub and the tip guard biased against the shaft of the needle.
Figure 8:
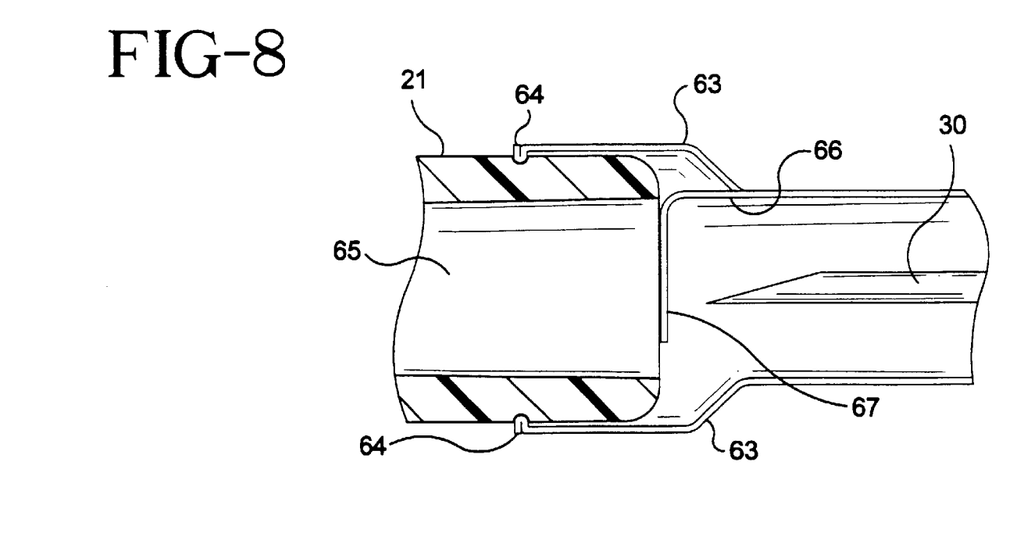
FIG. 8 is a cross-sectional view similar to FIG. 6, but showing the tip guard in an unbiased condition shielding the tip of the needle.

As shown most clearly in FIGS. 6 and 8, a tip guard 65 is securely mounted in coupler tube 60. Tip guard 65 is formed from a resilient material, preferably a stainless steel shim, and includes a mounting leg 66 securely mounted to coupler tube 60. Tip guard 65 also includes a shielding leg 67. Shielding leg 67 is biased away from mounting leg 65 generally perpendicular thereto. In the collapsed condition of the needle shield assembly, shielding leg 67 is moved to a position generally parallel to mounting leg 66 into sliding engagement with the shaft of needle 30. See FIG. 6. When needle 30 is withdrawn from catheter 20, and the interlocking telescoping tubes are in the fully extended and shielded position, shielding leg 67 will no longer abut the shaft of needle 30. In this manner, shielding leg 67 will be in its biased position covering the sharp distal tip of needle 30. See FIG. 8.

The clinician grips wing 27 to insert catheter and introducer needle assembly 10 into a patient. Because wing 27 is close to the distal tip of needle 30, insertion of catheter and introducer needle assembly 10 into a patient is relatively simple and the clinician can control catheter and introducer needle assembly 10 much easier than with prior catheter and needle assemblies. After catheter and introducer needle assembly 10 has been inserted into a vein, flashback of blood in needle 30 will be observed through notch 39 if catheter 20 is transparent or translucent. In addition, flashback of blood will be observed through the part of extension tube 24 that is in window 29 as long as at least this portion of extension tube 24 is transparent or translucent. Flashback of blood will be observed in window 29 because blood will exit notch 39, into catheter hub 21 and travel up extension tube 24 past window 29 because the path out of the proximal end of catheter hub 21 is blocked by elastomeric plug 26.

Upon proper positioning of catheter 22 in the patient's vein, a clinician using needle shield assembly 10 will exert a proximally directed force to shield housing 31 while holding catheter hub 21 in place. This initial proximally directed force will cause a proximal movement of needle 30 and shield housing 31 and will cause a telescoping of the interlocking telescoping tubes. More particularly, as noted above, the proximal end of needle 30 is adhered to shield housing 31 and the proximal end of anchor tube 40 is secured to shield housing 31 at glue port 32. Thus, the initial proximal movement of shield housing 31 will simultaneously draw needle 30 and anchor tube 40 in a proximal direction while coupler tube 60 remains connected to catheter hub 21. Sufficient proximal movement of needle 30, shield housing 31 and anchor tube 40 will cause outwardly extending locking flange 41 at the distal end of anchor tube 40 to engage inwardly extending locking flange 51 at the proximal end of intermediate tube 50. At the same time, lanced protrusions 52 ride over outwardly extending locking flange 41 so the proximal end of lanced protrusions 52 abut the distal face of outwardly extending locking flange 41.

Figure 10:
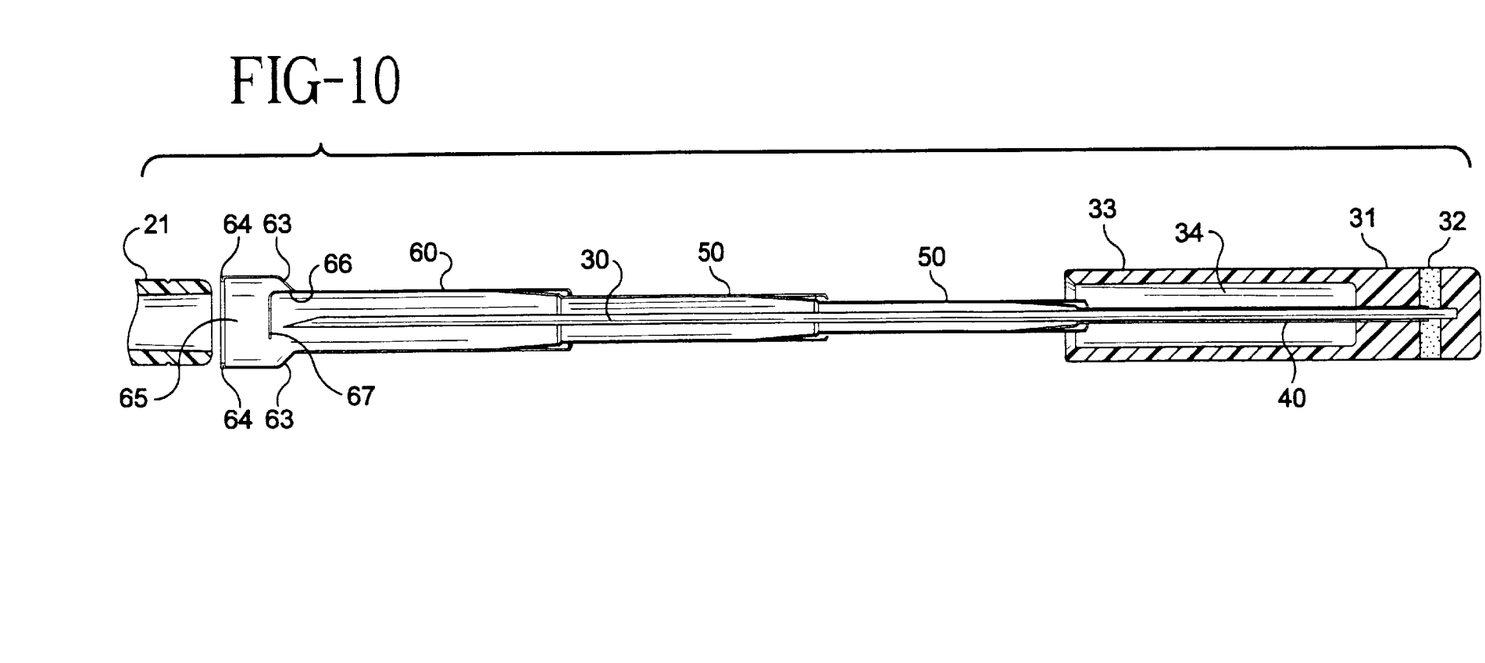
FIG. 10 is a cross-sectional view of the interlocking telescoping needle shield assembly of this invention shielding the needle after separation from the catheter hub with the tip guard in its unbiased condition shielding the tip of the needle.

Further proximal movement of anchor tube 40 will effectively pull intermediate tube 50 relative to shield housing 50. Further proximal movement of shield housing 31 causes locking flange 51 on the distal end of intermediate tube 50 to engage inwardly extending locking flange 61 at the proximal end of coupler tube 60 and prevents further extension between intermediate tube 50 and coupler tube 60. At the same time, lanced protrusions 62 ride over outwardly extending locking flange 51 so the proximal end of lanced protrusions 62 abut the distal face of outwardly extending locking flange 51. As needle 30 is moved further in a proximal direction, the sharp distal tip thereof will move proximally of shielding leg 67 of tip guard 65. Hence, shielding leg 67 will resiliently move toward an undeflected condition and will safely cover the sharp distal tip of needle 30 as shown in FIG. 8. Extension of shield assembly 30 beyond the FIG. 7 condition is prevented by engagement of the locking flanges as explained above. Hence, further proximally directed forces on shield housing 31 will overcome the mechanical interference fit between coupler tube 60 and catheter hub 21. Thus, as shown in FIG. 10, coupler tube 60 will slidably separate from catheter hub 21. In this separated condition, all portions of needle 30 are safely surrounded and shielded. Additionally, the lanced protrusions 52 and 62 effectively lock the interlocking telescoping tubes in the completely extended position to thereby prevent any possible re-exposure of needle 30. Shielding leg 67 also prevents any potential contact with the sharp distal tip of needle 30.

Thus, it is seen that a catheter assembly is provided that is "bloodless," that facilitates the verification of venipuncture, that includes a needle shield assembly that covers the entire needle as well as the sharp distal tip after use and is compact, simple and easy to use and does not require any special features or technique in order to be operative.

We claim:

1. A catheter and introducer needle assembly, comprising:
    a catheter having a proximal end and a distal end;
    a catheter hub in fluid communication with the catheter and having a proximal end and a distal end connected to the proximal end of the catheter and a side port in fluid communication with the catheter hub;
    a needle disposed in the catheter having a proximal end and a distal end;
    a shield housing securely connected to the proximal end of the needle;
    a plurality of nested tubes in sliding telescoping relation with one another where one of the tubes has a proximal end secured to the shield housing and another of the tubes has a distal end releasably engaged with the catheter hub;
    a lock associated with each tube to prevent relative movement between adjacent tubes once the adjacent tubes are locked in a fully extended position; and
    a plug affixed to the catheter hub and located proximal of the side port.

2. The catheter introducer set of claim 1 wherein each lock comprises a radially inwardly extending protrusion at a proximal portion of one tube and an outwardly extending flange at a distal portion of an adjacent tube.

3. The catheter introducer set of claim 2 wherein the coupling tube includes a plurality of fingers along a distal portion thereon that engage the catheter hub.

4. The catheter introducer set of claim 3 wherein the catheter hub further includes a circumferential groove therein to engage the plurality of fingers.

5. The catheter introducer set of claim 3, further comprising a needle tip guard mounted in the coupling tube and being slidable along the needle as the plurality of nested tubes are extended with respect to one another, the tip guard being biased to move over the distal end of the needle when the plurality of nested tubes are in a fully extended condition.

6. A catheter and introducer needle assembly comprising:
    a catheter having a proximal end and a distal end;
    a catheter hub in fluid communication with the catheter and having a proximal and a distal end connected to the proximal end of the catheter and a side port in fluid communication with the catheter hub;
    a needle disposed in the catheter having a sharp distal tip and a proximal end with at least one notch located in the needle to allow fluid flow therethrough;
    a shield housing connected to the proximal end of the needle; and
    a plurality of tubes operatively connected to the shield housing wherein the plurality of tubes include means for preventing separation of the tubes and means for preventing collapse of the tubes once the tubes have been extended.

7. The needle shield assembly of claim 6 further comprising a means associated with the plurality of tubes for releasably connected the needle shield assembly to a catheter hub.

8. The needle shield assembly of claim 7 further comprising a means for covering the sharp distal tip of the needle when the plurality of nested tubes have been extended.

9. The needle shield assembly of claim 6 further comprising a means for covering the sharp distal tip of the needle when the plurality of nested tubes have been extended.

10. A catheter and introducer needle assembly, comprising:
    a catheter having a proximal end and a distal end;
    a catheter hub in fluid communication with the catheter and having a proximal and a distal end connected to the proximal end of the catheter and a side port in fluid communication with the catheter hub;
    a needle disposed in the catheter having a sharp distal tip and a proximal end with at least one notch located in the needle to allow fluid flow therethrough;
    a shield housing connected to the proximal end of the needle;
    an anchor tube having a proximal end and a distal end disposed about the needle and having its proximal end connected to the shield housing and an outwardly extending flange adjacent the distal end;
    at least one intermediate tube disposed about the anchor tube and having a proximal end with an inwardly extending flange and a distal end with an outwardly extending flange and wherein at least one inwardly biased protrusion extends from a proximal portion of the intermediate tube;

a coupler tube disposed about the intermediate tube and having a proximal end with an inwardly extending flange and at least one inwardly biased protrusion; and a plug affixed to the catheter hub and located proximal of the side port and the notch.

11. The needle shield assembly of claim 10 further comprising a plurality of fingers extending from the distal end of the coupler tube and being adapted to removably engage a catheter hub.

12. The needle shield assembly of claim 11 further comprising a tip guard connected to the coupler tube and being slidable along the needle as the coupler tube, intermediate tube and anchor tube are extended with respect to one another, the tip guard being biased to move over the sharp distal tip of the needle once the coupler tube, intermediate tube and anchor tube have been fully extended with respect to one another.

13. The needle shield assembly of claim 10 further comprising a tip guard connected to the coupler tube and being slidable along the needle as the coupler tube, intermediate tube and anchor tube are extended with respect to one another, the tip guard being biased to move over the sharp distal tip of the needle once the coupler tube, intermediate tube and anchor tube have been fully extended with respect to one another.

* * * * *